(12) United States Patent
Zhan et al.

(10) Patent No.: US 12,032,115 B2
(45) Date of Patent: Jul. 9, 2024

(54) GLASS-METAL OR CERAMIC-METAL SEALED TWO-PIECE MICROWAVE COAXIAL SENSOR AND PLACEMENT AT A VERTICAL VENTURI

(71) Applicant: Schlumberger Technology Corporation, Sugar Land, TX (US)

(72) Inventors: Linyuan Zhan, Singapore (SG); Cheng-Gang Xie, Singapore (SG); Muhammad Fuad Bin Mohamed Zain, Singapore (SG); Mengke Zhan, Singapore (SG); Jianhua Zhu, Singapore (SG); Guillaume Jolivet, Singapore (SG)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 18/343,967

(22) Filed: Jun. 29, 2023

(65) Prior Publication Data

US 2023/0341581 A1    Oct. 26, 2023

Related U.S. Application Data

(63) Continuation of application No. 17/249,368, filed on Mar. 1, 2021, now Pat. No. 11,733,420.

(30) Foreign Application Priority Data

Feb. 28, 2020    (SG) ............................ 10202001816R

(51) Int. Cl.
*G01F 1/58* (2006.01)
*E21B 49/08* (2006.01)
(Continued)

(52) U.S. Cl.
CPC ............ *G01V 3/30* (2013.01); *E21B 49/0875* (2020.05); *G01F 1/58* (2013.01); *G01F 1/74* (2013.01)

(58) Field of Classification Search
CPC ......... G01V 3/30; E21B 49/0875; G01F 1/58; G01F 1/74; G01F 1/44; G01F 7/00; G01F 15/18; G01N 22/00; G01N 33/246
See application file for complete search history.

(56) References Cited

U.S. PATENT DOCUMENTS 6,831,470 B2    12/2004    Xie et al.
9,638,556 B2    5/2017    Xie et al.
(Continued)

*Primary Examiner* — Christopher P McAndrew
*Assistant Examiner* — Zannatul Ferdous
(74) *Attorney, Agent, or Firm* — Jeffrey D. Frantz

(57) ABSTRACT

Electromagnetic probes for analyzing a flowing multi-phase fluid are described herein. The probes generally use a probe assembly for measuring liquid properties in a multiphase fluid flowing in a conduit, the probe assembly comprising a first member with a probe portion and a connection portion, the probe portion having a central bore with a conductor and a pressure-resistant insulator surrounding the conductor, the conductor extending from an opening at a distal end of the probe portion into the connection portion, the connection portion having a connector coupled to a distal end of the connection portion, the connection portion having a seal face with a groove extending around the probe portion; and a second member that, when assembled, is in direct contact with the first member at the distal end of the connection portion to apply compression and to retain the first member against a wall of the conduit.

20 Claims, 10 Drawing Sheets

(51) Int. Cl.
  *G01F 1/74*     (2006.01)
  *G01V 3/30*     (2006.01)

(56)           References Cited

U.S. PATENT DOCUMENTS

| | | |
|---|---|---|
| 10,330,622 B2 | 6/2019 | Noel et al. |
| 10,648,841 B1 * | 5/2020 | Arsalan .................... G01F 1/74 |
| 11,733,420 B2 * | 8/2023 | Zhan ................... E21B 49/0875 |
| | | 324/338 |
| 2007/0220987 A1 * | 9/2007 | Clifton ...................... G01F 1/44 |
| | | 73/736 |
| 2016/0169720 A1 * | 6/2016 | Xie ......................... G01F 1/582 |
| | | 73/861.11 |
| 2018/0143052 A1 * | 5/2018 | Xie ...................... E21B 49/087 |

* cited by examiner

GLASS-METAL OR CERAMIC-METAL SEALED TWO-PIECE MICROWAVE COAXIAL SENSOR AND PLACEMENT AT A VERTICAL VENTURI

CROSS-REFERENCE TO RELATED APPLICATIONS

This application is a continuation of U.S. application Ser. No. 17/249,368, filed on Mar. 1, 2021, which claims the benefit of Singapore Patent Application Serial No. 10202001816R filed on Feb. 28, 2020. Each of the above applications is incorporated herein by reference in its entirety.

BACKGROUND

Field

This disclosure relates to multiphase flow measurement devices and more particularly to multiphase-flow electromagnetic microwave reflection sensors that may be used standalone or with multiphase flow meters at downhole, surface, or subsea locations.

Description of the Related Art

Wells are generally drilled into subsurface rocks to access fluids, such as hydrocarbons, stored in subterranean formations. The subterranean fluids can be produced from these wells through known techniques. Operators may want to know certain characteristics of produced fluids to facilitate efficient and economic exploration and production. For example, operators may want to know flow rates of produced fluids. These produced fluids are often multiphase fluids (e.g., those having some combination of water, oil, and gas), making measurement of the flow rates more complex.

Various systems can be used to determine flow rates for multiphase fluids. In some systems, multiphase fluids are separated into their constituent phases and these phases are then individually measured by using single-phase flow meters to determine flow rates. Other systems include multiphase flow meters that can be used to measure flow rates of multiphase fluids without separation. These multiphase flow meters may be smaller and lighter than traditional separators equipped with single-phase flow meters, and the ability to measure flow rates without separation may be desirable in some instances. Both the traditional separator systems and the multiphase flow meter systems can also be used to determine certain other fluid characteristics of interest.

It is also desirable to determine properties of the multiphase mixture, such as the presence, fraction, and salinity of water in the mixture, and the water-in-liquid ratio, as this provides information about produced and/or injected water in the mixture, about the (subsea) flow-assurance measures needed to prevent hydrate formation and/or pipeline corrosion, and may affect other measurements being made on the multiphase mixture. Microwave sensors for the measurement of multiphase flows can be used with multiphase flow meters to determine water salinity, water fraction, and water-in-liquid-ratio (WLR or water-cut).

The use of electromagnetic (EM) methods, such as microwaves, has been suggested because of their high measurement sensitivity to the presence of the water phase in a multiphase flow (water permittivity/conductivity is much higher than the permittivity/conductivity of the hydrocarbon oil-gas phases). For example, U.S. Pat. No. 6,831,470, assigned to Schlumberger, shows that the fluid-contacting front-end of a microwave open-ended coaxial probe (an EM sensor) has a pressure-integrity glass-to-metal seal acting as a first pressure barrier (where the glass is a good electrical insulator, or low-loss dielectric material). The back-end of the probe may have an integral N-type connector of 50-ohm characteristic impedance. The measurement probe front-aperture is mounted flush with the pipe wall of a measurement pipe section. The probe is connected through the N-type connector to the microwave electronics housed in an explosion-proof enclosure by the use of a short microwave coaxial cable/adaptor with no pressure barrier. A bulky and sometimes expensive enclosure is needed as a second pressure barrier to contain the process fluids in case the pressure-barrier formed by the probe's glass-to-metal seal fails.

U.S. Pat. No. 9,638,556, issued to Schlumberger (entitled "Compact microwave water-conductivity probe with integral second pressure barrier"), describes methods and devices for measuring fluid properties by using an electromagnetic (EM) sensor. The electromagnetic sensor includes a coaxial probe body having a first integral pressure barrier and a second integral pressure barrier formed from coaxial-feedthrough connector. The first integral pressure barrier and the second integral pressure barrier have a desired characteristic impedance.

U.S. Pat. No. 10,330,622, issued to Schlumberger (entitled "Glass-sealed electrode"), describes an electrode (a coaxial probe) that includes a (center) conductor, an insulator (such as glass), and a metallic housing. The insulator is positioned at least partially around the conductor. The housing is positioned at least partially around the insulator. An upper surface of the insulator may be at least partially concave, an outer surface of the housing may have a groove formed therein, or both.

SUMMARY

Embodiments described herein provide a probe assembly for measuring liquid properties in a multiphase fluid flowing in a conduit, the probe assembly comprising a first member with a probe portion and a connection portion, the probe portion having a central bore with a conductor and a pressure-resistant insulator surrounding the conductor, the conductor extending from an opening at a distal end of the probe portion into the connection portion, the connection portion having a connector coupled to a distal end of the connection portion, the connection portion having a seal face with a groove extending around the probe portion; and a second member that, when assembled, is in direct contact with the first member at the distal end of the connection portion to apply compression and to retain the first member against a wall of the conduit.

Other embodiments provide an apparatus for analyzing a flowing multiphase fluid, the apparatus comprising a conduit; and an open-ended microwave probe assembly disposed in fluid communication with the conduit through a wall of the conduit, the conduit having a first coupling structure, the probe assembly comprising a first member with a probe portion and a connection portion, the probe portion having a central bore with a conductor and a pressure-resistant insulator surrounding the conductor, the connection portion having a coaxial connector coupled to a distal end of the connection portion and connected to the conductor, the connection portion having a seal face with a groove extending around the probe portion, and a seal member disposed in the groove, the probe portion extending through the first coupling structure and the seal face of the connection portion in sealing contact with the wall of the conduit; and a second member having a second coupling structure for engaging with the first coupling structure.

Other embodiments provide a method of analyzing liquid properties of a flowing multiphase fluid, the method comprising disposing an open-ended microwave probe assembly in a port formed in a flow containment structure of a flow system carrying the flowing multiphase fluid, the port having a first coupling structure, the probe assembly comprising a first member with a probe portion and a connection portion, the probe portion having a central bore with a concentric conductor and a pressure-resistant insulator surrounding the concentric conductor, the connection portion having a connector coupled to a distal end of the connection portion and connected with the concentric conductor, the connection portion having a seal face with a groove extending around the probe portion, and a seal member disposed in the groove, the seal face of the connection portion in sealing contact with a wall of the flow containment structure; and a second member having a second coupling structure that couples with the first coupling structure to apply compression to the distal end of the connection portion to seal the seal face against the wall of the flow containment structure; and energizing the concentric conductor by applying radio frequency energy to the connector.

BRIEF DESCRIPTION OF THE DRAWINGS

Certain embodiments of the disclosure will hereafter be described with reference to the drawings, wherein like reference numerals denote like elements. It should be understood, however, that the accompanying drawings illustrate only the various implementations described herein and are not meant to limit the scope of various technologies described herein. The drawings show and describe various embodiments of the current disclosure.

DETAILED DESCRIPTION

Figure 1:
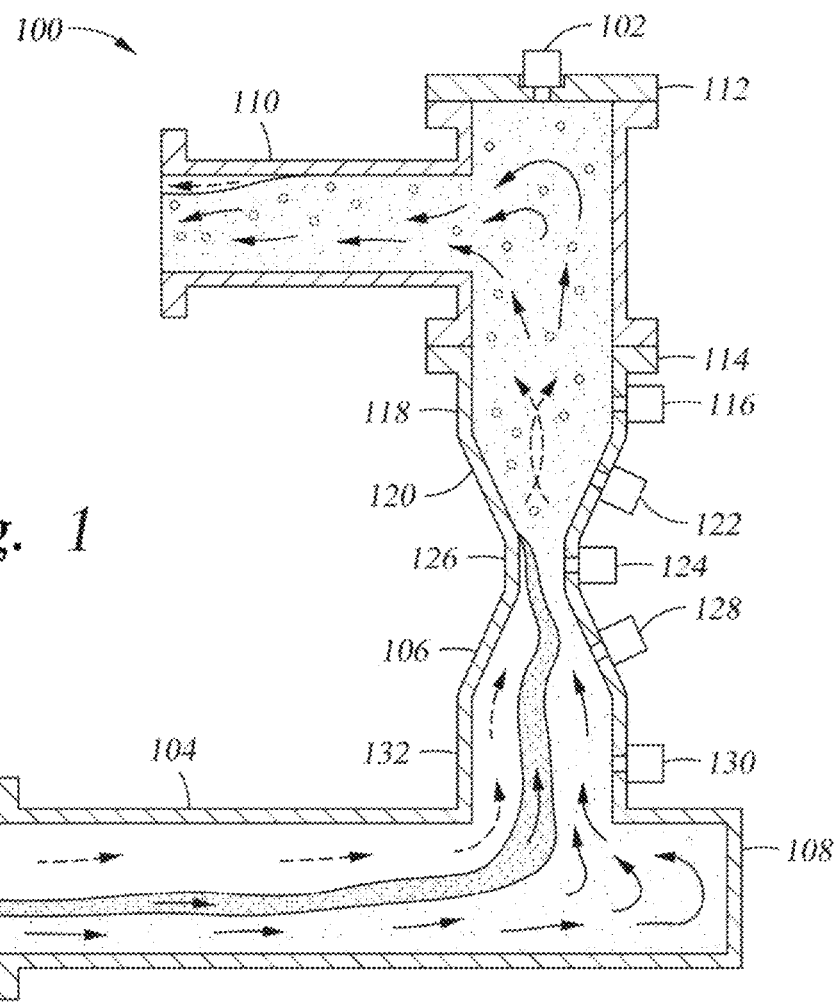
FIG. 1 shows a flow measurement apparatus for analyzing flow of a multiphase fluid.

In the following description, numerous details are set forth to provide an understanding of the present disclosure. It will be understood by those skilled in the art, however, that the embodiments of the present disclosure may be practiced without these details and that numerous variations or modifications from the described embodiments may be possible.

In the specification and appended claims: the terms "connect", "connection", "connected", "in connection with", and "connecting" are used to mean "in direct connection with" or "in connection with via one or more elements"; and the term "set" is used to mean "one element" or "more than one element". Further, the terms "couple", "coupling", "coupled", "coupled together", and "coupled with" are used to mean "directly coupled together" or "coupled together via one or more elements". As used herein, the terms "up" and "down", "upper" and "lower", "upwardly" and "downwardly", "upstream" and "downstream"; "above" and "below"; and other like terms indicating relative positions above or below a given point or element are used in this description to more clearly describe some embodiments of the disclosure.

Electromagnetic sensors, such as microwave open-ended coaxial probes, for water property detection of multiphase flows may be used with multiphase flow meters to determine water conductivity or salinity, water fraction, and water-in-liquid-ratio (WLR or water-cut). To improve the detectability of the onset of first water and changes in the water conductivity (salinity) or changes in the concentration of a hydrate-inhibitor in water, it has been discovered through multiphase-flow experimental studies that an electromagnetic microwave sensor or sensor(s) may be installed in the liquid-rich locations of a blind-tee inlet arrangement. A blind-tee inlet is often used as a flow-mixing pipework for a vertically-installed multiphase flowmeter, such as a multiphase flow meter based on Venturi meter and multi-energy gamma-ray measurement section, or an electrical impedance measurement section, or a microwave transmission-resonance measurement section.

In one embodiment, a two-piece microwave coaxial probe or electromagnetic sensor has a single short or long pressure barrier (insulator) embedded in the (probe body) front piece (first member). The front piece has an alloy (e.g., Inconel) body and a concentric conductor (made of e.g. cemented carbide), bonded by single short or long glass- or ceramic-metal seal(s) (insulator). The microwave coaxial probe or electromagnetic sensor is designed to have a desired characteristic impedance (e.g. ca. 50 Ohms). The front of the probe flat or concaved e.g. glass surface aperture is in direct contact with process fluid and is substantially flush-mounted at the inner-wall liquid-rich region of a flow containment structure. An appropriately-designed protruding feature (wall member) may be incorporated near the front aperture for local liquid enrichment. An off-the-shelf radio frequency (RF) coaxial connector is attached to and in good electrical coupling with the probe's concentric conductor and affixed to the back end (connection portion) of the front piece, such as by screws. The back piece (second member) is designed to provide compressive support to the front piece in the case of face seal (seal face) so that a C-ring or an O-ring (seal member) on the front piece can be squeezed against the outer pipe wall of a pressure vessel/pipeline body and seal against process flow pressure (e.g., 5000 psi). A rod/piston seal is another possibility to seal against pressure. The back piece itself is fixed to the pressure vessel/pipeline body by, for example, a single (e.g., M33) thread or by a multiple-bolt back flange.

An electromagnetic (EM) sensor may be used to determine the Water Liquid Ratio (WLR) and water salinity of oil-water-gas multiphase flows in an upstream oil-gas production pipeline. The system is based on microwave reflection measurement method and the EM sensor is to transmit microwave signal (generated by an appropriate electronics circuitry located away from the probe assembly) and detect (using the same circuitry) the reflected microwave signal with the multiphase flow. The EM sensor sensing aperture, with a flat or concaved insulator (e.g. glass) surface, is in direct contact with high pressure, high temperature and corrosive process flow. The front sensing aperture of the EM sensor is substantially flush-mounted at the near inner-wall (locally liquid-rich) region of the pipeline section in order to make good WLR and brine salinity measurements. The EM sensors for performing microwave reflection measurement may be based on open-ended coaxial probe design with glass-metal or ceramic-metal high-pressure seals, such as those disclosed in U.S. Pat. Nos. 9,638,556 and 10,330,622, issued to Schlumberger.

FIG. 1 shows a flow measurement apparatus 100 for analyzing flow of a multiphase fluid. Several locations are shown where an EM sensor can be installed at various locations of one or more flow containment structures, such as a conduit, blind pipe, or flange, in a flow system to yield good WLR and brine salinity measurements of the flowing multiphase fluid. A first EM sensor 102 is shown installed at a top blind flange 112 downstream of a vertical upflowing Venturi 114 (Venturi acts as a flowmeter as well as a good flow mixer); the well-mixed oil-water liquid is enriched at the top blind flange location by the blind flange 112 where the first EM sensor 102 is installed. Liquid tends to collect near the blind flange 112 as the flow changes direction to exit through an outlet conduit 110. However, this location may not be desirable in some cases where the vertical blind flange (and the EM sensor and its electronics enclosure) needs to be removed to provide access for the flowmeter system (such as one based on Venturi and gamma-ray). A second EM sensor 116 is shown installed on the side wall 118 (in substantial azimuthal alignment with the bottom horizontal blind-tee 108) downstream of the divergent section 120 of the vertical Venturi 114. A third EM sensor 122 can be installed in the divergent section 120, on side wall 118 at the tapered portion thereof. Thus, one or more EM sensors can be installed in a wall of a Venturi device at a divergent section thereof. A fourth EM sensor 124 can be installed at the throat section 126 of the Venturi 114, near the divergent section 120 where flow velocity/oil-water mixing is at the highest, if the throat section 126 of the Venturi 114 is sufficiently long to allow installation of the EM sensor 124. Computational fluid dynamics modelling and experimentation have revealed that a thicker liquid wall layer can be found at the inlet section and the convergent section, upstream of the throat section, of a Venturi device, for example at the Venturi inlet after the right-angle turn of a bottom blind 108 in an inlet line 104, in substantial azimuthal alignment with the bottom blind 108, which may be a blind pipe or flange. A fifth EM sensor 128 can be installed at the side wall 118 at the convergent section 106 of the Venturi 114, in the tapered portion thereof and substantially azimuthally aligned with the blind 108. A sixth EM sensor 130 can be installed at the Venturi inlet section 132, upstream of the convergent section 106 and substantially azimuthally aligned with the blind 108. The sixth EM sensor 130 located at the Venturi inlet will measure a thicker liquid layer than that located at the Venturi convergent section 106, which is advantageous for the EM sensor to achieve good water salinity and WLR measurements over a wider gas-volume-fraction (GVF) range. The fifth and sixth EM sensors 128 and 130 can be installed non-invasively at the convergent and inlet sections of the Venturi 114 so that fluid flow into the Venturi 114, and any resulting differential pressure measurements thereof, would not be disrupted by the sensors. The fifth and sixth EM sensors 128 and 130 can be installed at the blind pipe 108 so that fluid flow into the Venturi 114, and any resulting differential pressure measurements thereof, would not be disrupted by the sensors. Any combination of one or more of the EM sensors 102, 116, 122, 124, 128, and 130 can be used, depending on the needs of individual processes.

The side wall EM sensor locations at Venturi throat 126, at the divergent section 120, or downstream of the divergent section 120 may have a decreased amount of liquid near pipe walls at high GVF (wet-gas) conditions, leading to a reduced capability to detect early water, brine salinity and to measure the WLR accurately. A liquid-enrichment means local to the front aperture of the EM sensor may be desirable in some embodiments. It should also be noted that, in some cases, an EM sensor may be used with a vertical straight pipe section (without a Venturi device) downstream of a horizontal blind pipe; the second to sixth EM sensor positions may have little difference in terms of the amount of near-wall liquid. A liquid-enrichment means local to the front aperture of the EM sensor may or may not be used in such cases.

The body of the front piece may be made of $H_2S$-resistant alloy such as Inconel. The center conductor (coaxial or concentric conductor) may be made of Inconel or Cemented Carbide (also $H_2S$ resistant). The glass- or ceramic-seal insulator material may be appropriately chosen (such as borosilicate glass, solar glass, alumina ceramic or the like) to withstand the desired process pressure and temperature, be resistant to salts and various chemicals in produced fluids, and to have stable dielectric constant and low electrical loss. The inner diameter of the probe body and the outer diameter of the center conductor are sized appropriately, together with the dielectric constant of the seal material (including a coaxial conductor-insulator insert in the probe body for use with a short glass-metal seal, FIG. 3A), to form a coaxial transmission-line structure of a desired characteristic impedance, such as 50 Ohm. The coefficients of thermal expansion of the probe body, the concentric conductor and the insulator are appropriately chosen to achieve insulator-to-metal pressure seal.

Figure 2:
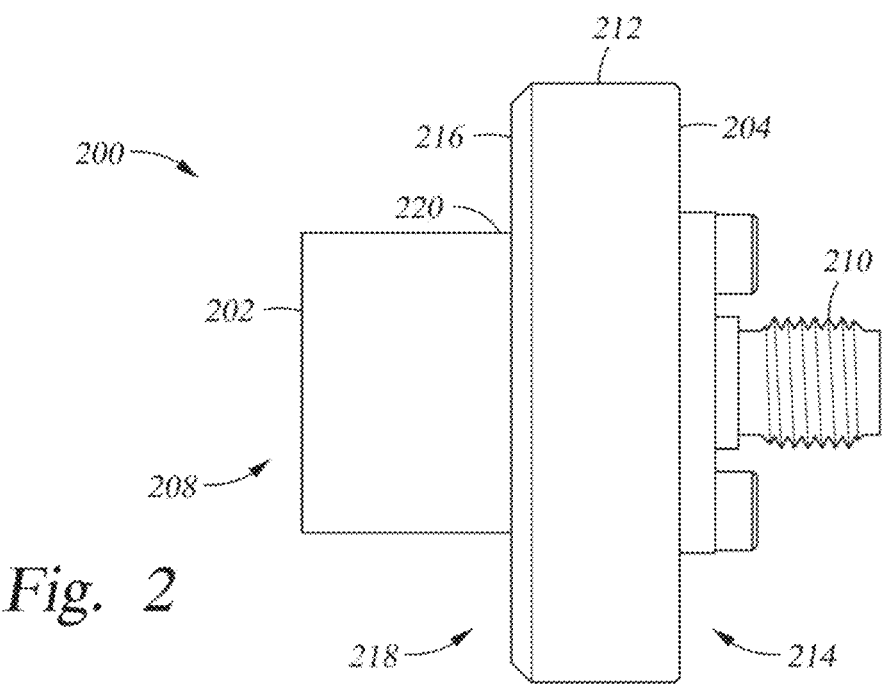
FIG. 2 is an elevation view of a front piece for an EM probe assembly, according to one embodiment.

FIG. 2 is an elevation view of a front piece 200, according to one embodiment. The front piece 200, made of Inconel, has a probe portion 202 and a connection portion 204 for connecting to RF sources. An appropriately chosen off-the-shelf RF connector 210, here a coaxial connector, may be attached to the connection portion 204.

The connection portion 204 of the front piece 200 has a seal face 216 that faces the probe portion 202 in the axial direction of the front piece 200. The seal face 216 has a groove 218 (not visible in FIG. 2) that extends around a proximal end 220 of the probe portion 202 to accommodate a seal member (not shown) in the groove 218. The seal face 216, and seal member disposed therein, are for sealing around a port into which the probe portion 202 extends to expose the probe (not shown) within the probe portion to the flowing fluid.

Figure 3A:
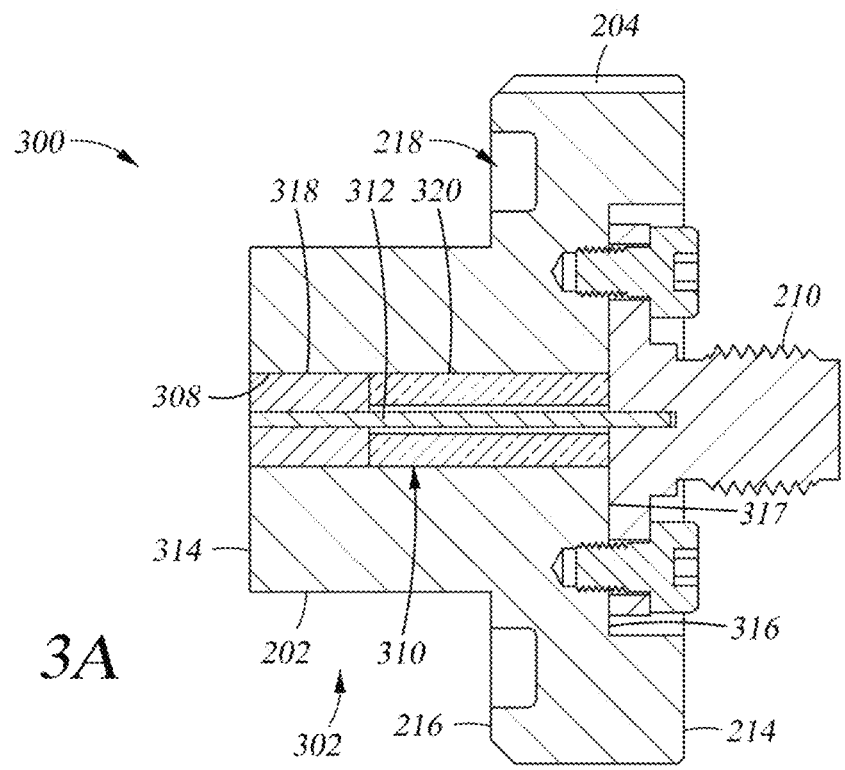
FIG. 3A is a cross-sectional view of a front piece for an EM probe assembly according to another embodiment.

FIG. 3A is a cross-sectional view of a front piece 300 for an EM probe assembly according to another embodiment. The front piece 300 is similar to the front piece 200 of FIG. 2 in many ways. The front piece 300 has the probe portion 202 and the connection portion 204, which together define a probe housing 302. The connector 210 is attached to the probe housing 302 at the connection surface 214. Here, a recess 316 formed in the connection surface 214 accommodates the connector 210, but the connector 210 can be attached to a flat (i.e. un-recessed) connection surface 214, as in FIG. 2. The connector 210, which may be a standard off-the-shelf RF connector, is fastened to the connection portion 204, in this case using bolts or screws.

The probe housing 302 has an axial bore 308 that houses an insulation assembly 310 and a probe 312, which may be a center or a concentric conductor, and made from for example an appropriate-material metal pin with a suitable outer diameter. The axial bore 308 is disposed through the probe housing 302 from a first end 314 of the probe housing to a second end 317 of the probe housing, opposite from the first end. The axial bore 308 is formed through the probe housing 302 such that a central axis of the probe housing 302 is coincident with an axis of the axial bore 308. The insulation assembly 310, in this case, has a first insulator 318 and a second insulator 320, both of which are disposed in the axial bore 308 surrounding the probe 312. The probe 312 is an electrical conductor that is disposed within the insulation assembly 310, in a passage formed through the first and second insulators 318 and 320 of the insulation assembly 310, along an axis thereof, which is substantially coincident with the axis of the insulation assembly 310 and the probe housing 302, from the first end 314 of the probe housing 302 to the second end 317, and beyond into the connector 210 to allow electric power, for example RF power, to be connected to the probe 312. At least one of the first and second insulators 318 and 320 has an outer radius substantially the same as an inner radius of the axial bore 308 so that the insulation assembly 310 can seal the axial bore 308 against process fluids, to which the probe 312 is exposed when the front piece 300 is installed in an operating facility, for example in a conduit or flow structure. In this case, the first insulator 318 is a short glass-metal seal and the second insulator 320 is a coaxial conductor-insulator. Ceramic-metal material can be used in place of glass-metal for the first insulator 318. The first insulator 318 is here configured to contact the probe 312 and the inner wall of the axial bore 308 to seal the axial bore 308, and the second insulator 320 may be configured with a small cylindrical gap around the probe 312 between the probe 312 and the second insulator 320, as shown here, to maintain a characteristic electrical impedance of the probe 312. The length of the first insulator 318 and the second insulator 320 may be selected according to appropriate design criteria. The probe housing 302 has the seal face 216, with the groove 218 for accommodating a seal member. Here, the probe housing 302 is shown without a liquid enhancement feature such as the wall member 402 shown in FIG. 4A. A liquid enhancement feature may be added to the probe housing 302, if desired.

Figure 3B:
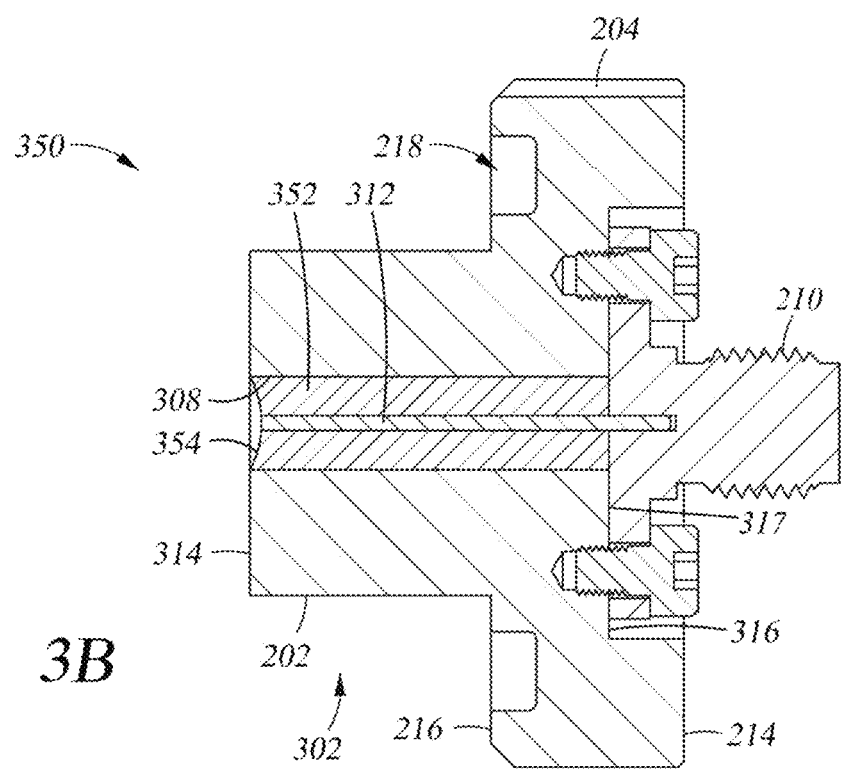
FIG. 3B is a cross-sectional view of a front piece for an EM probe assembly according to another embodiment.

FIG. 3B is a cross-sectional view of a front piece 350 according to another embodiment. The front piece 350 is similar to the front piece 300 and the front piece 200 in most respects. The front piece 350 has a single insulator 352, instead of the insulation assembly 310 of FIG. 3A. The insulator 352 is a glass-metal (or ceramic-metal) insulator disposed in the axial bore 308. The insulator 352, in this case, extends from the first end 314 of the probe housing 302 to the second end 317, and contacts the connector 210. The insulator 352 has a concave surface 354 at the first end 314 of the probe housing 302 to minimize stress-induced cracking of the insulator 352. The concave surface 354 is recessed within the first end 314, and the probe 312, in this case, is open to process fluids at a slightly recessed position relative to the first end 314 of the probe housing 302. The depth of the recess is typically 0.1 to 0.5 mm.

Figure 4A:
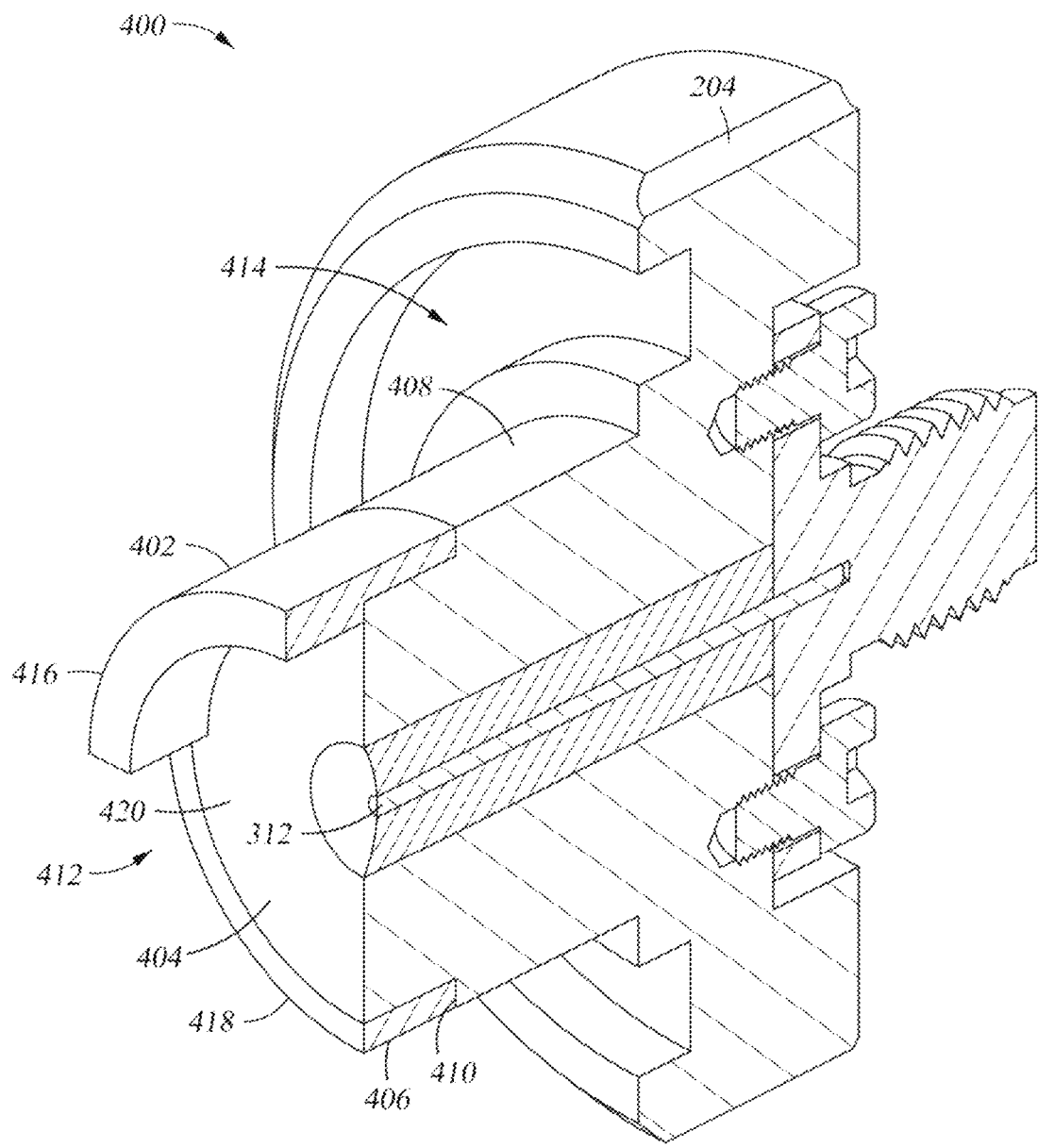
FIGS. 4A-4C are perspective cross-sectional views of other different embodiments of a front piece for an EM probe assembly.

FIG. 4A is a perspective cross-sectional view of a front piece 400 according to another embodiment. The front piece 400 is similar to the front piece 350 of FIG. 3B, and to the front pieces 300 and 200, in most respects. In this case, the front piece 400 has a wall member 402 that is removable. The wall member 402 provides liquid enhancement by creating a turn in flow of the multiphase fluid to encourage fluids to coagulate according to density differences. The front piece 400 has a probe portion 404 with a first section 406 and a second section 408. The first section 406 has a first outer radius and the second section 408 has a second outer radius larger than the first outer radius. The first section 406 extends in an axial direction of the front piece 400 from a first end 412 of the probe portion 404 to the second section 408. The second section 408 extends from a second end 414 of the probe portion 404, at the connection portion 204, to the first section 406. The first section 406 and the second section 408 meet at a wall 410 that extends radially outward from the first section 406 to the second section 408. In this case, the wall 410 extends only in a radial direction, but in some cases, the wall 410 may also extend some distance in the axial direction to form a frustoconical wall.

The removable, replaceable, wall member 402 is disposed around the first section 406 and has a wall portion 416 that extends beyond the first end 412. The wall portion 416 extends from a ring portion 418 of the wall member 402. The wall portion 416 extends partway around the circumference of the ring portion 418 to form, in this case, a cylindrical wall. When installed in a flow system such as that of FIG. 1, the wall member 402 is generally oriented such that the wall portion 416 is located at a downstream, relative to a flow path of the flowing multiphase fluid, of the probe portion 404. The wall portion 416 forces the flowing multiphase fluid to turn to encourage liquid to collect near the first end 412 of the probe portion 404. Enhancing the presence of liquid at the first end enhances detection and analysis of liquid properties in the flow multiphase fluid.

Here, as an illustration, the wall portion 416 has an inner radius that is less than the first outer radius of the first section 406 of the probe portion 404, such that the wall portion 416 partially overlaps an end surface 420 of the probe portion 404, at a peripheral region thereof. The ring portion 418 has an axial length substantially equal to an axial length of the first section 406 of the probe portion 404, such that the ring portion 418 substantially covers the outer cylindrical surface of the first section 406. The ring portion 418 has an outer radius that is substantially the same as an outer radius of the wall portion 416, such that an outer surface of the ring portion 418 and an outer surface of the wall portion form a continuous outer surface. The outer surface of the wall portion 416 and the ring portion 418 have a radius that is, in this case, substantially the same as the second outer radius of the second section 408 of the probe portion 404. In this case, therefore, the outer surface of the second section 408 and the outer surface of the ring portion 418 and the wall portion 416 form a surface with substantially constant outer radius. Because the wall portion 416 overlaps a portion of the end surface 420 of the probe portion 404, the ring portion 418 has an inner radius larger than the inner radius of the wall portion 416.

Figure 4B:
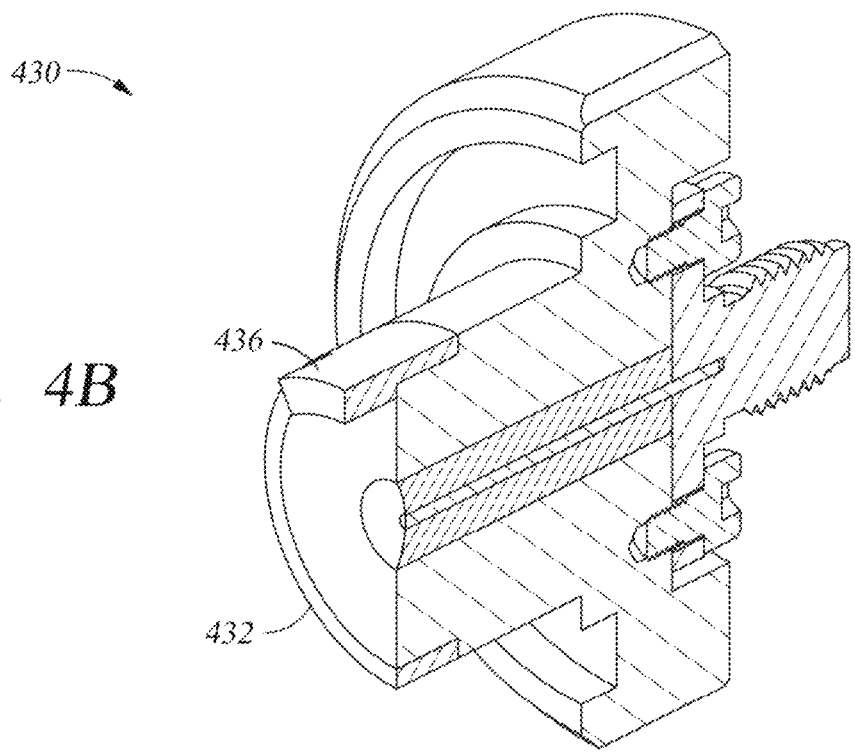

The wall member 402 is removable by sliding the wall member 402 off the end of the first section 406 of the probe portion 404. By making the wall member 402 removable and replaceable, other wall members having different configurations can be used for liquid enhancement to correspond with different desired process features. FIG. 4B is a perspective cross-sectional view of a front piece 430, according to another embodiment. The front piece 430 has a removable wall member 432, according to another embodiment. The wall member 432 is similar to the wall member 402 of FIG. 4A. The front piece 430 and the front piece 400 have the same probe housing, illustrating how a plurality of removable, replaceable wall members can be used for liquid enhancement with one probe housing. The wall member 432 has a wall portion 436 with a smaller angular extent than the wall portion 416 of the wall member 402 of FIG. 4A.

The wall portion 416 is shown here as a cylindrical extension protruding outward from the first end 412 of the probe portion 404. Alternative configurations can be used for liquid enhancement. The wall portion 416 can be flat, rather than curved, or curved in a non-cylindrical manner. The wall portion 416 can have a flat wall with end tabs that extend at angles from the wall, for example at right angles. The wall portion 416 is shown here extending directly outward from the first end 412 in a direction parallel to the axial direction of the front piece 400. In other embodiments, the wall portion 416 can extend in a direction that is not parallel to the axial direction, but instead makes an angle with the axial direction. For example, depending on the needs of an individual process, the wall portion 416 might angle toward or away from the probe 312. The wall portion 416 is shown here as a continuous wall, but alternative configurations can use a discontinuous wall. Gaps or holes can be provided in the wall portion 416 at convenient locations in some embodiments, while other embodiments might use rod-like extensions, parallel to, perpendicular to, or forming another angle with, the axial direction of the front piece 400 to form a partial or discontinuous wall. The wall portion 416 is also shown here as having a rectangular profile when viewed toward the broad side of the wall portion 416. Alternative configurations might use a wall with a curved profile when viewed from that direction. Liquid enhancement can be obtained using any type of protrusion that provides a local turning or recirculation of the fluid flow to encourage collection of liquid near the probe 312. The wall member 402 may be oriented such that the wall portion 416 is located at an upstream location, relative to a flow path of the flowing multiphase fluid, of the probe portion 404.

Orientation of the wall member 402 can be aided by an orientation feature (not shown) that can be provided in the ring portion 418 of the wall member 402, with a corresponding, matching, orientation feature (not shown) provided in the outer wall of the first section 406 of the probe portion 404 to engage with the orientation feature of the wall member 402. The orientation features can be matching bumps, ridges, recesses, grooves, and the like. Alternately, orientation of the wall member 402 may be secured by use of a fastener, such as a grub screw (not shown).

Figure 4C:
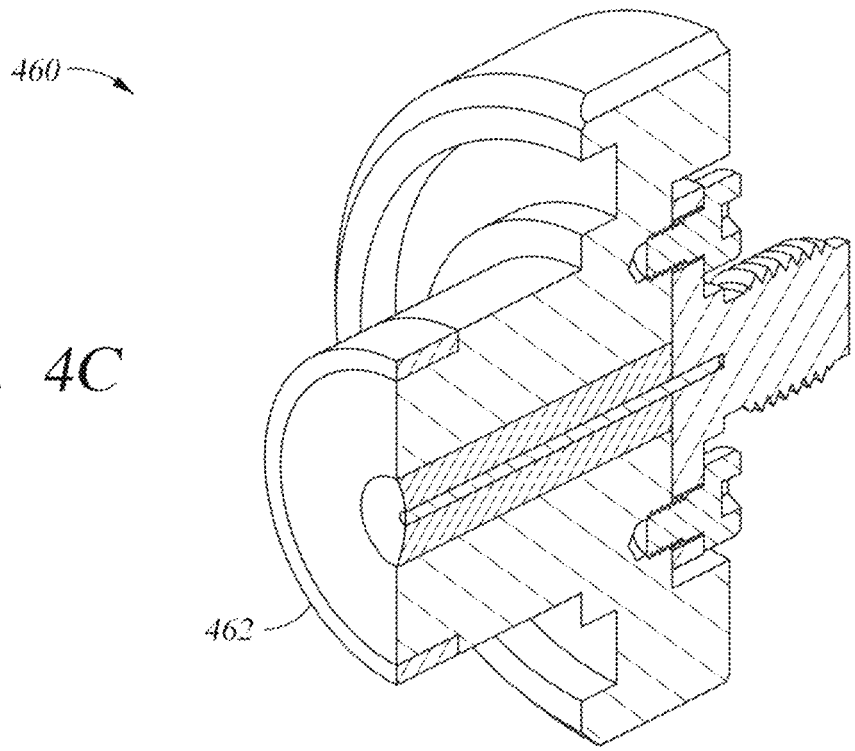

FIG. 4C is a perspective cross-sectional view of a front piece 460, according to another embodiment. The front piece 460 has the same probe housing as the front piece 430 and the front piece 400, with the probe portion 404 that can receive a removable member. In this case, a ring member 462 is disposed around the first section 406 of the probe portion 404. The ring member 462 is not a liquid enhancement feature, having no wall portion to protrude into the fluid flow. The ring member 462 can be used at times when no liquid enhancement is desired to fill the gap between the first section 406 of the probe portion 404 and the inner wall of the port into which the front piece 460 is inserted. The ring member 462 prevents unwanted materials, such as sand and other solids, from collecting in the gap by filling the gap.

The wall members 402 and 432, and the ring member 462, can be made of any convenient material. In some cases, a low cost erosion-resistant thermoplastic, such as polyether ether ketone (PEEK), can be used. Metals, erosion-resistant ceramics, and composites, can also be used. The members can be molded, cast, sculpted, or 3-D printed using appropriate materials. An alignment feature (not shown), such as a groove, ridge, bump, notch, pin, grub screw, or other appropriate feature, can be formed in, or provided for, any of the members 402, 432, and 462, as needed. It should be noted that a ring member, such as the ring member 462, may have other functional features that benefit from orientation, even though the ring member 462 does not have a liquid enrichment wall portion. It should also be noted that, instead of using a removable, replaceable wall member, the first portion of the front pieces 200, 300, 350, 400, 430, and/or 460 could have an integral wall portion that extends along the axial direction of the front piece away from the respective first ends of the probe portions thereof. In such embodiments, the front piece itself can have orientation features to help orient the wall portion according to fluid flow direction. The orientation features can be provided in the probe portion or the connection portion of the front piece.

Reduction in the complexity and cost of the EM coaxial probe sensor for use with a desired design pressure such as 5000 psi may also be desired. This may be accomplished by removing an integral coaxial feedthrough with a second glass-metal or ceramic-metal seal (as disclosed in U.S. Pat. No. 9,638,556). A polished concaved front (glass) surface at a probe body (front piece) may be needed for a long e.g. glass-metal seal design (FIG. 3B) to avoid stress-induced fine cracks forming in glass (as disclosed in U.S. Pat. No. 10,330,622). Reducing the amount of expensive (Inconel) alloy used for the probe body (front piece) and avoiding having a circumferential groove (as disclosed in U.S. Pat. No. 10,330,622) may also be desirable.

Figure 5:
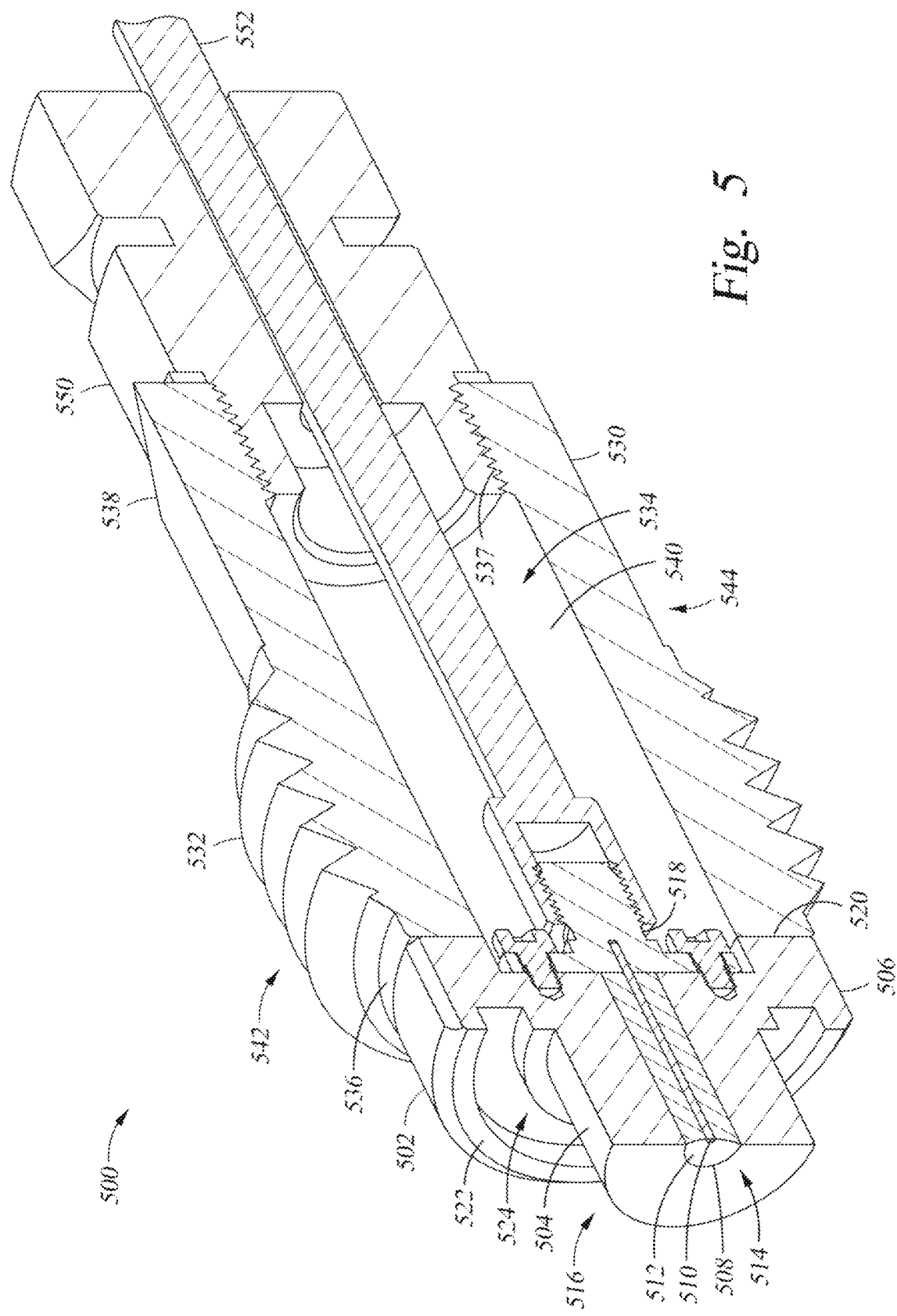
FIG. 5 is a perspective cross-sectional view of a probe assembly according to one embodiment.

FIG. 5 is a perspective cross-sectional view of a probe assembly 500 according to one embodiment. The probe assembly 500 has a first member 502 with a probe portion 504 and a connection portion 506, similar to the front pieces described above. The probe portion 504 has a central bore 508 with a probe 510, shown as a concentric and/or coaxial conductor here, and a pressure-resistant insulator 512 surrounding the probe 510, similar to the front piece 350. Here, the pressure-resistant insulator 512 is of the long length variety described in connection with FIG. 3B. The probe 510 extends from an opening 514 at a distal end 516 of the probe portion 504 into the connection portion 506. The probe 510, which may be a coaxial conductor, is exposed at the opening 514 to contact process fluids for analysis thereof. The connection portion 506 has a connector 518 coupled to a distal end 520 of the connection portion 506 and a seal face 522 with a groove 524 extending around the probe portion 504. The seal face 522 here is the same as the seal face 216 of FIG. 2, but can be configured in any convenient way. The connector 518 is substantially the same as the connector 210, but any convenient connector can be used here. The groove 524 accommodates a resilient seal member, such as an O-ring or C-ring, that can be inserted into the groove 524. When pressed against a pipe wall around an opening for the probe portion 504, the seal member seals the opening. Here, the first member 502 has no liquid enhancement feature, such as the removable wall member 402

The probe assembly 500 has a second member 530 shown engaged with the first member 502. The second member 530 is a conduit member that has an external thread 532 and an internal passage 534 from a first end 536 of the second member 530 to a second end 538 of the second member 530 opposite from the first end 536, the internal passage 534 having a smooth wall 540 at the first end 536 and an internal thread 537 at the second end 538. The internal thread 537 can be used to couple to a cable gland 550 for securing an RF cable 552. The second member 530 has a first portion 542 with a first outer radius, the first portion 542 bearing the external thread 532, and a second portion 544 with a second outer radius that is less than the first outer radius in this illustration. Here, the second portion 544 is unthreaded along the outer wall, but any features, such as a hexagonal cross-section, can be incorporated into the outer wall of the second portion 544 as needed, for example to facilitate applying torque to the second member 530 to engage the threads 532 with a threaded port (not shown) to apply compression and retain the first member 502.

The second member 530 is shown engaged with the first member 502 in an operating configuration. When installed, the second member 530 directly contacts the first member 502, and the external thread 532 of the second member engages with a threaded bore. The seal face 522 of the first member 502 contacts a pipe wall, flange, or other flow containment structure, and progressive engagement of the external thread 532 of the second member 530 presses the first member 502 against the flow containment structure to form the seal around the probe portion 504.

The first member 502 can be a front piece, as described in connection with FIGS. 2-4C, and the second member 530 can be a back piece. The second member 530 holds the first member 502 in place with the probe portion 504 protruding through an opening in a flow containment structure, such as a pipe wall or flange. Engagement of the external thread 532 of the second member 530 provides a sealing force between the seal face 522 and the flow containment structure to press the seal member (not shown) in the groove 524 against the flow containment structure, thus providing compressive support to the first member 502. The internal passage 534 provides a conduit for the RF cable 552, here a coaxial cable, to make electrical connection to the connector 518. The probe 510, here a center conductor, extends through the first member 502 into the connector 518 to make RF connection.

Figure 6:
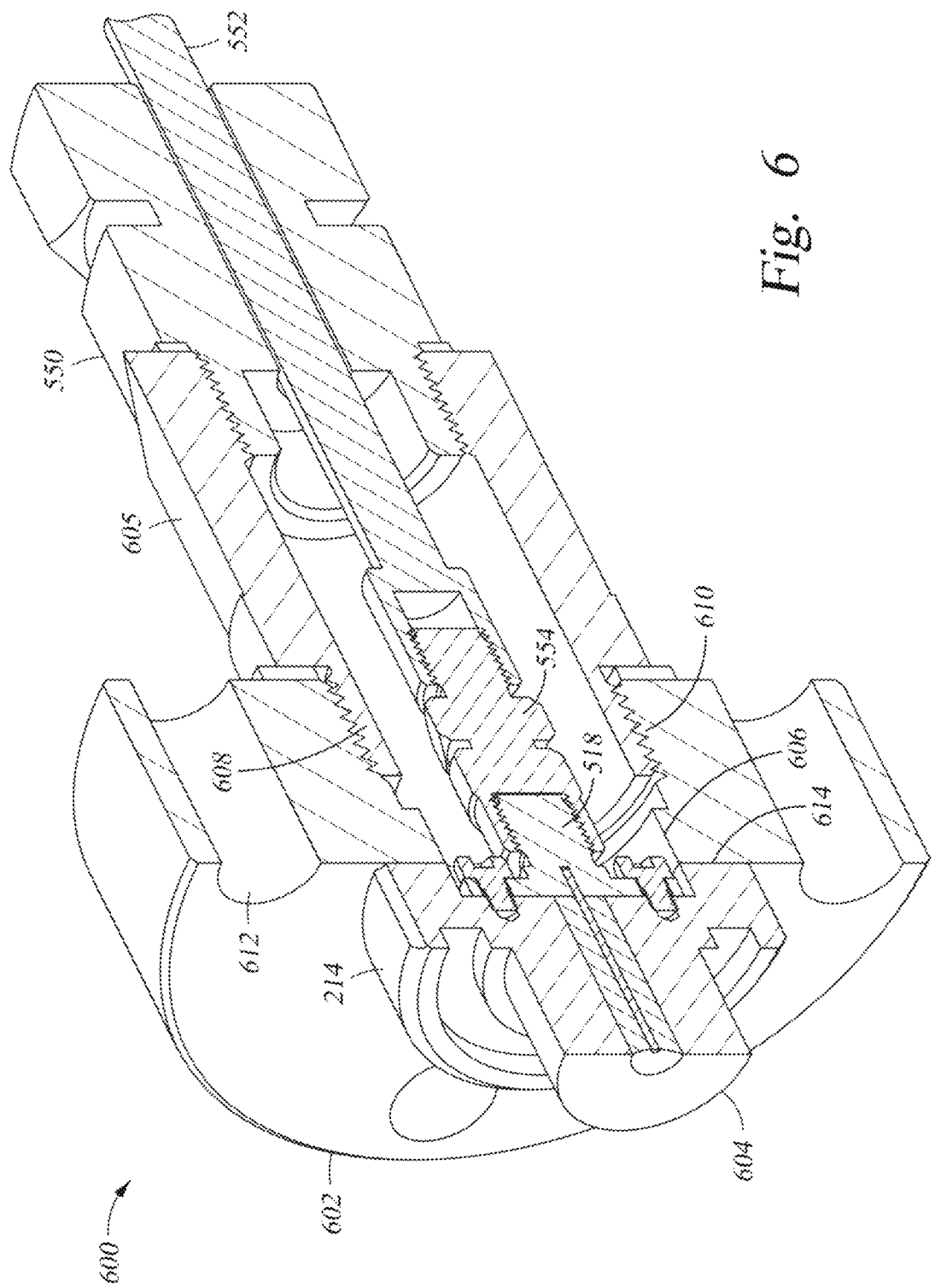
FIG. 6 is a perspective cross-sectional view of a probe assembly according to another embodiment.

FIG. 6 is a perspective cross-sectional view of a probe assembly 600 according to another embodiment. In this case, the probe assembly 600 uses a flange member 602 for attachment to a flow containment structure. The probe assembly 600 uses a first member 604 similar to the front piece 350 of FIG. 3B with a conduit member 605 that serves as a holding gland and conduit for the RF cable 552 that connects to the connector 518. Here, the flange member 602 is the second member that applies compression to the first member 604 against the conduit wall to seal the port. The flange member 602 has an internal bore 606 formed through the flange member 602 in an axial direction thereof to provide access to the connector 518 for connection of the RF cable 552. The conduit member 605 has an external thread 608 that engages with an internal thread 610 formed in the bore 606. The RF cable 552 may engage directly with the connector 518, or as shown here an adaptor 554 may be used to connect the RF cable 552 with the connector 518. When installed, the flange member 602 makes direct contact with the first member 604, at a distal end 614 of the connection portion 204, and is bolted to the flow containment structure at bolt holes 612 to provide sealing force between the seal face 522 and the flow containment structure. The cable gland 550 can also be used here.

It should be noted that in some embodiments, the flange member 602 and conduit member 605 may be one second member, a unitary object. In such cases the second member would have a flange portion and a conduit portion that extends axially from a center of the flange portion. In general, the probe assemblies described herein have a first member with a probe portion that is disposed through an opening in a conduit (or flange, or blind pipe) for exposure to a flowing fluid. The conduit has a first coupling structure, so that a second member of the probe assembly can couple with the first coupling structure to apply pressure to the first member of the probe assembly. The second member may generally comprise a flange. Additionally, or instead, the second member may comprise a conduit. The second member can be a conduit member, a flange member, a combination of a conduit member and a flange member, or a unitary object that has a flange portion and a conduit portion. The second member generally has a second coupling structure for coupling with the first coupling structure to enable application of compression to the first member. Engagement of the coupling structures is illustrated below.

Figure 7:
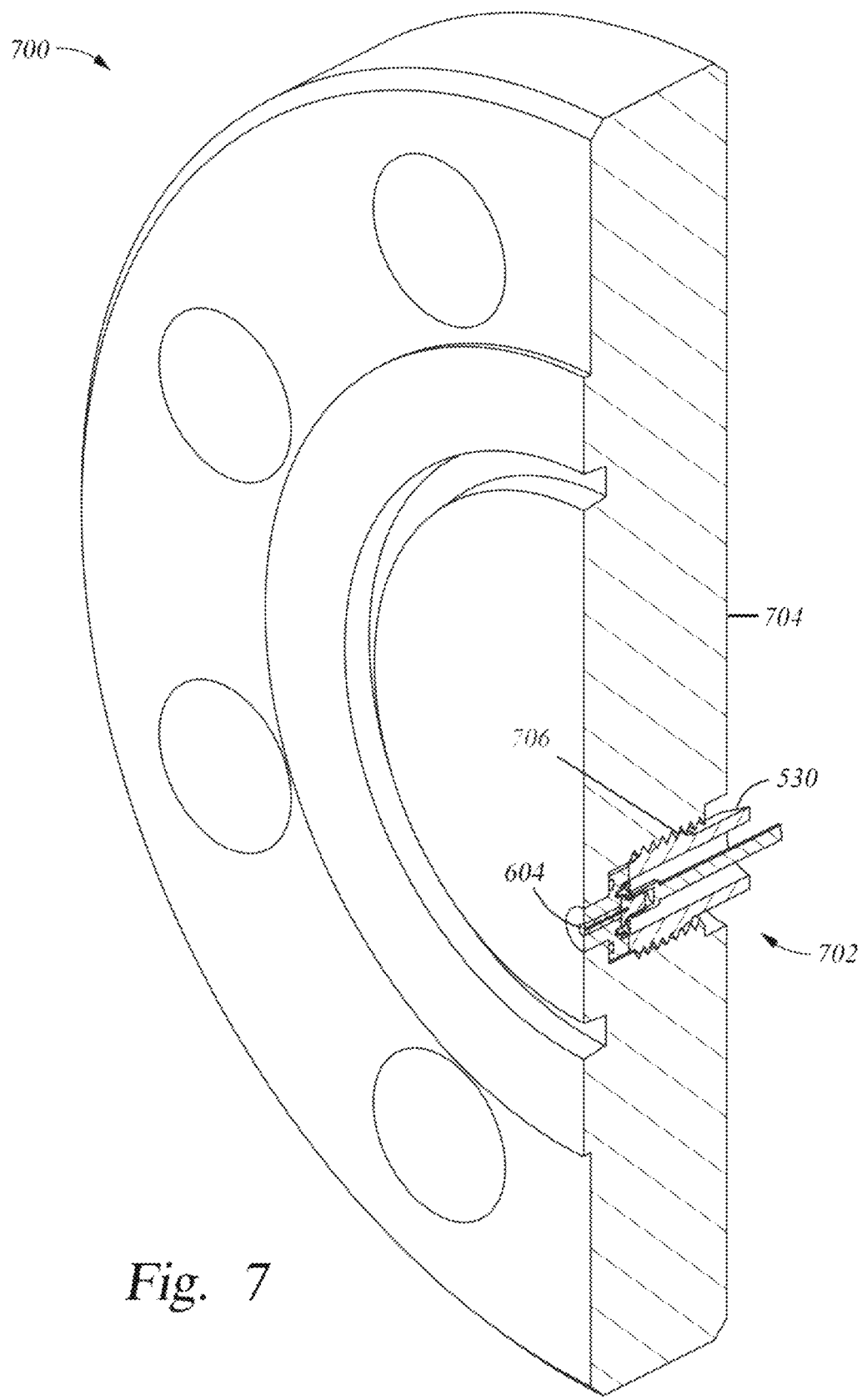
FIGS. 7-9 are perspective cross-sectional views of different apparatus embodiments for analyzing a flowing multiphase fluid.

FIG. 7 is a perspective cross-sectional view of an apparatus 700 for analyzing a flowing multi-phase fluid. The apparatus 700 has a probe assembly 702 with the first member 604 and the second member 530 installed in a flange 704 as the flow containment structure. The probe assembly 702 is here installed off-center in the flange 704 to illustrate the flexibility of locating the probe assembly 702 at any convenient liquid-rich location of the flow containment structure. The apparatus 700 can be installed as the first EM sensor 102 of FIG. 1.

Here, the first coupling structure is a threaded port 706, through which the probe portion of the first member 604 is disposed. The second member 530, here a conduit member, has a second coupling structure that is an external thread for coupling with the first coupling structure to apply compression to the first member 604 against the wall of the conduit, in this case a shelf of the bore into which the probe portion is extended.

Figure 8:
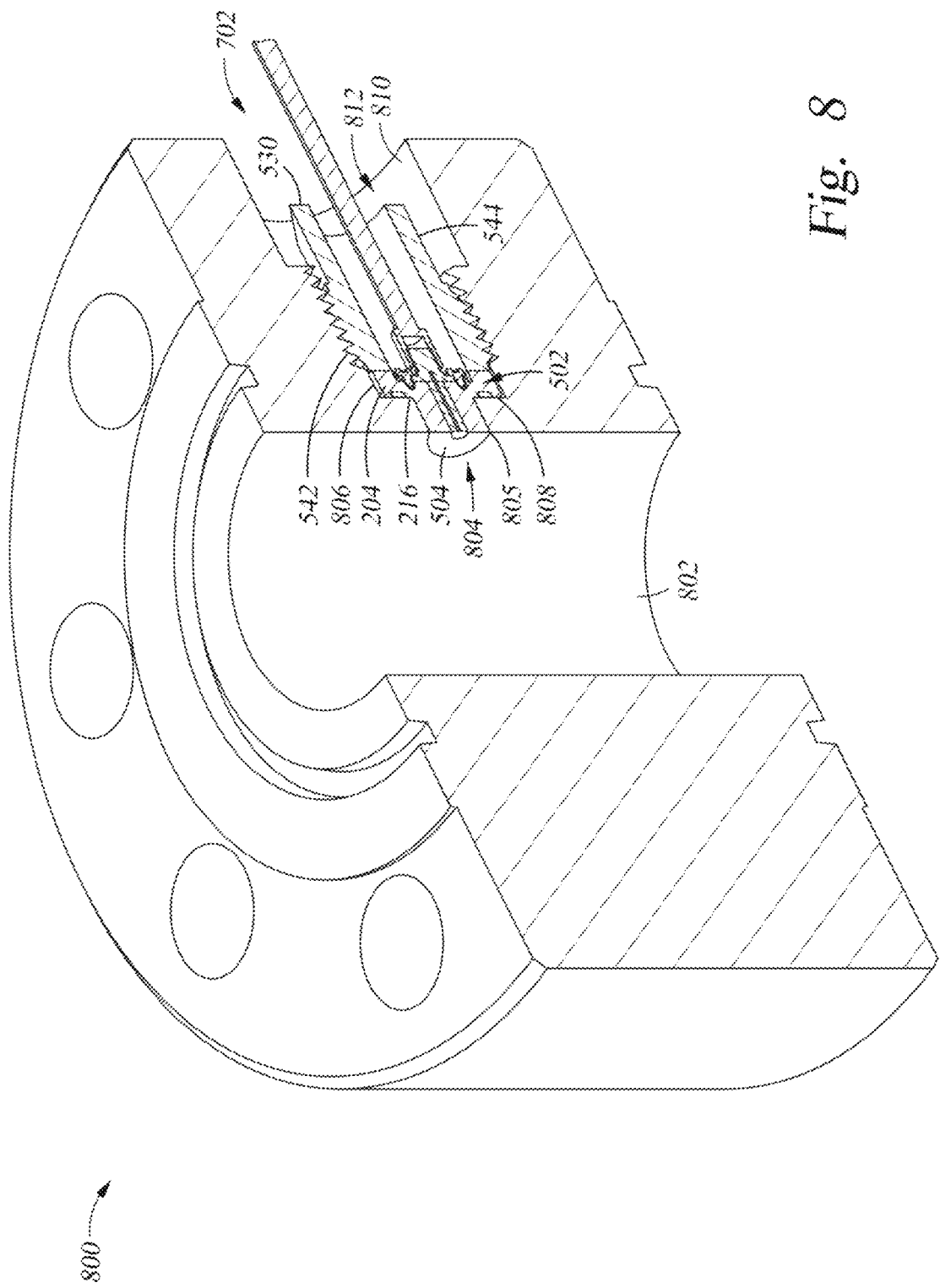

FIG. 8 is a perspective cross-sectional view of an apparatus 800 for analyzing a flowing multiphase fluid. In this case, the probe assembly 702 is installed through the side of a tubular flow containment structure 802, which may be a flange or pipe wall. The first member 502 is disposed in a port 804 formed in the flow containment structure 802 that has three sections. A first section 805 admits the probe portion 504 into contact with the flowing multiphase fluid. A second section 806 houses the connection portion 204 and the first portion 542 of the second member 530. The second section 806 has an internal thread as the first coupling structure to engage with the external thread 532 of the first portion 542 as the second coupling structure. The second section 806 meets the first section 805 at a shelf 808 that contacts the seal face 216 of the connection portion 204. As noted above, the second member 530 presses the seal face 216 of the first member 502 against the shelf 808. The second section 806 may have an inner radius that is larger than an inner radius of the first section 805. A third section 810 of the port 804 may have an inner radius that is larger than the inner radius of the second section 806, forming an annular gap 812 between the third section 810 of the port 804 and the second portion 544 of the second member 530 to provide access to install and remove the second member 530.

Figure 9:
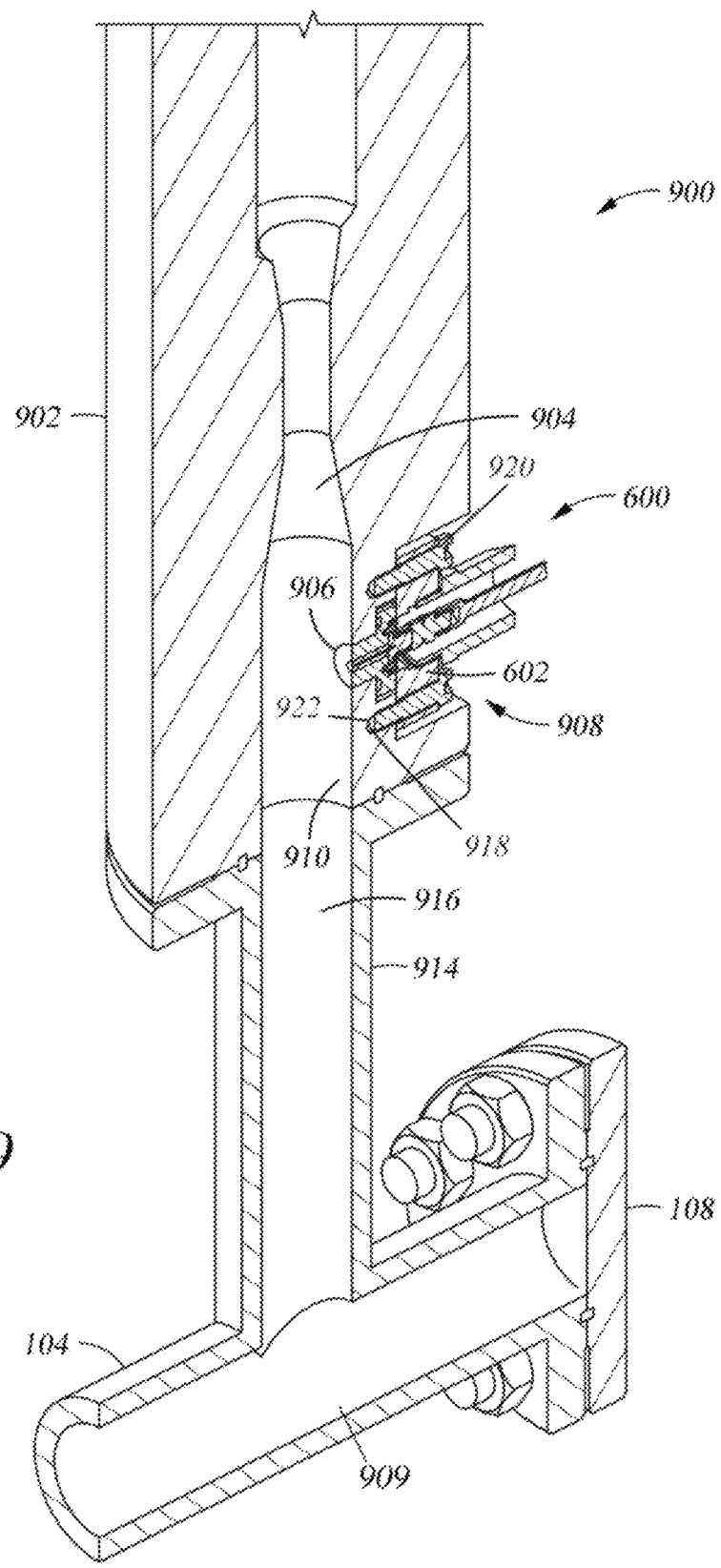

FIG. 9 is a perspective view of an apparatus 900 for analyzing a flowing multi-phase fluid according to another embodiment. Here, the probe assembly 600 is installed in a pipe wall upstream of the convergent section 904, at an inlet section 910, of a Venturi device 902, as a flow containment structure. The probe assembly 600 is installed non-invasively to the fluid flow. The probe assembly 600 is substantially azimuthally aligned with a horizontal blind-tee 909 of the inlet pipe 104 to the Venturi device 902. At the inlet section 910, on the side of the blind-tee 909, a layer of liquid of the multiphase fluid is thicker than that along the wall opposite from the probe assembly 600. As fluid flows from the inlet 104 into the vertical flow pipe 914, the change in flow direction encourages fluids of different densities to segregate in an interior 916 of the pipe 914, with higher density liquid tending to collect along the wall of pipe 914 closest to blind-tee 909. A port 906 formed in the flow containment structure has a fastening section 908 that accommodates the flange member 602 as a back flange for bolting directly to the pipe wall. In this case, the first coupling structure is a plurality of bores 918 formed in the wall of the inlet section 910, and the second coupling structure is a plurality of holes 920 in the flange member 602, and a plurality of fasteners 922, in this case bolts, disposed through the holes 920 into the bores 918. Here, the probe assembly 600 is shown with no local liquid enhancement to minimize flow disruption at the inlet of the Venturi device 902. In this embodiment, the horizontal end blind-tee 909 and the vertical flow pipe 914 extending from the blind-tee 909 and inlet pipe 104 to the Venturi device 902 act as liquid (or liquid fraction) enhancement structure, because the liquid layer that accumulates along the side of the vertical pipe 914 in which the probe assembly 600 is installed is thicker than along the wall opposite from the probe assembly 600, and such contrast in liquid richness continues into at least the inlet section of the Venturi device 902.

Figure 10:
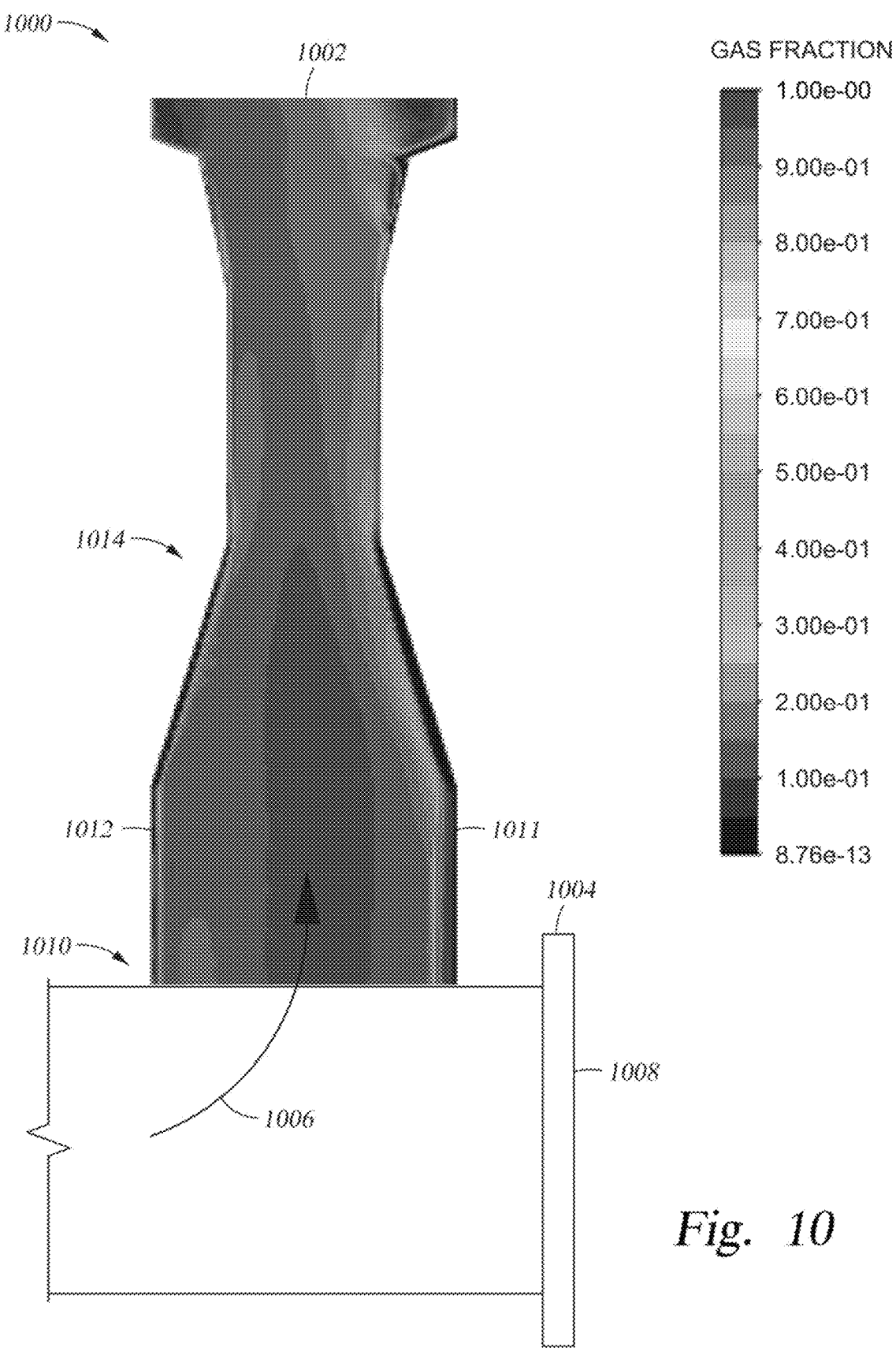
FIG. 10 is a graphical depiction of a multiphase fluid flowing in a Venturi device measurement apparatus, the graphical depiction showing liquid content at different locations in the multiphase fluid.

FIG. 10 is a graphical depiction 1000 of a multiphase fluid 1002 flowing in a measurement apparatus or a Venturi device 1014 coupled to a blind-tee section 1010 having a blind flange 1008, the graphical depiction showing 1000 liquid content of the multiphase fluid at different locations along the vertical Venturi 1014. This graphical depiction is in color to allow viewing of the different liquid contents. Fluid flow is in the direction of arrow 1006. Here, as the gas-fraction legend indicates, thicker liquid layers form along the side 1011 of the vertical Venturi 1014 that is aligned with the blind flange 1008 of the blind-tee 1010 installed upstream of an inlet of the Venturi device 1014. Thinner liquid layers appear along the opposite side 1012 of the Venturi device 1014. The model that gave rise to the graphical depiction 1000 indicates that installation of EM probes at the locations of the fifth and sixth EM probes 128 and 130 of FIG. 1 can successfully engage with a liquid-rich layer for reliable analysis of the multiphase fluid.

The EM probes, probe assemblies, and flow systems shown herein generally use a method of analyzing a flowing multiphase fluid for determining water properties such as water conductivity or salinity and WLR, the method including disposing an open-ended microwave probe assembly of the sort described herein in a port, which may be threaded, formed in a flow containment structure carrying the flowing multiphase fluid, and energizing the probe assembly using radio frequency (RF) energy. The probe assembly is generally located at or near a liquid-rich region of the flow containment structure. A liquid fraction enhancement structure may be used; the liquid enhancement structure is a structure of the flow system that encourages liquid to collect near a wall region of the flow containment structure. As noted above, enhancement of the amount or fraction of liquid in the flow improves analysis of the liquid. The liquid fraction enhancement structure, such as a horizontal end blind-tee to vertical pipe transition, typically changes a flow direction of the multiphase fluid, allowing density differences of the liquid and gas phases to aggregate the liquids and gases, at least to an extent. In some cases, a local liquid enhancement structure can be provided as part of the probe assembly to enhance collection of liquid at the open end of the probe assembly. A single probe assembly can be installed in a flow system, or multiple probe assemblies can be used to compare results. Comparing results can be helpful in improving quality and repeatability of data from the probes, and different probe assemblies can be used to focus on different aspects of the multiphase fluid flow.

The EM probes described herein are frequently shown in azimuthal alignment with a blind section of a blind-tee to capture liquid fraction enhancement resulting from a turning of the fluid flow. It should be noted that the azimuthal alignment does not have to be absolute alignment. The alignment can be substantial, so that a few angular degrees of misalignment is tolerated. Liquid fraction enhancement is generally found along the inner wall on the side of the conduit nearest the blind section since that side of the conduit is along the outer radius of the turn in the flow path of the fluid. An EM probe can be installed out of absolute alignment with the blind section, and can find liquid enhancement along the inner wall on the "blind side" of the conduit.

Although the preceding description has been described herein with reference to particular means, materials and embodiments, it is not intended to be limited to the particulars disclosed herein; rather, it extends to all functionally equivalent structures, methods, and uses, such as are within the scope of the appended claims.

What is claimed is:

1. A probe assembly to measure liquid properties in a multiphase fluid flowing in a conduit, the probe assembly comprising:
a first member with a probe portion and a connection portion, the probe portion having a central bore with a conductor and a pressure-resistant insulator surrounding the conductor, the conductor extending from an opening at a distal end of the probe portion into the connection portion, the connection portion having a connector coupled to a distal end of the connection portion, the connection portion having a seal face with a groove extending around the probe portion; and
a second member that, when assembled, is in direct contact with and circumferentially covers the first member at the distal end of the connection portion to apply compression to the first member to retain the first member against a wall of the conduit.

2. The probe assembly of claim 1, wherein the second member has a threaded wall.

3. The probe assembly of claim 2, wherein the second member has a first portion, the threaded wall being an external wall of the first portion, and a second portion having a feature incorporated into an outer wall of the second portion to facilitate applying torque to the second member.

4. The probe assembly of claim 1, further comprising a removable wall member that surrounds the distal end of the probe portion and has a wall portion that extends from a portion of the removable wall member.

5. The probe assembly of claim 1, wherein the first member comprises a corrosion-resistant metal material, the conductor comprises a corrosion-resistant material, and the pressure-resistant insulator is a glass or ceramic material.

6. The probe assembly of claim 1, wherein the first member, the conductor, and the insulator are made of materials chosen to have coefficients of thermal expansion that promote insulator-to-metal pressure seal.

7. The probe assembly of claim 1, wherein the second member is selected from a flange member, a combination of a flange member and a conduit member, or a unitary member having a flange portion and a conduit portion.

8. An apparatus to analyze a flowing multiphase fluid, the apparatus comprising:
an open-ended microwave probe assembly disposed in fluid communication with a conduit through a wall of the conduit, the conduit having a first coupling structure, the probe assembly comprising:
a first member with a probe portion and a connection portion, the probe portion having a central bore with a conductor and a pressure-resistant insulator surrounding the conductor, the connection portion having a coaxial connector coupled to a distal end of the connection portion and connected to the conductor, the connection portion having a seal face with a groove extending around the probe portion, and a seal member disposed in the groove, the probe portion extending through the first coupling structure and the seal face of the connection portion in sealing contact with the wall of the conduit; and
a second member having a second coupling structure to engage with the first coupling structure at the distal end of the connection portion, wherein the second member circumferentially covers the first member to apply compression to the first member to retain the first member against the wall of the conduit.

9. The apparatus of claim 8, wherein the first coupling structure is a threaded port, the second member is a conduit member, and the second coupling structure is an external thread on an outer wall of the second member.

10. The apparatus of claim 9, wherein the first coupling structure is a plurality of bores formed in the wall of the conduit, the second member comprises a back flange, and the second coupling structure is a plurality of holes in the back flange and a plurality of fasteners disposed through the holes and into the bores.

11. The apparatus of claim 8, wherein the conduit comprises a blind-tee, and the open-ended microwave probe assembly is disposed at a location of the conduit that is azimuthally aligned with a blind portion of the blind-tee.

12. The apparatus of claim 8, further comprising a wall member that surrounds a distal end of the probe portion and has a wall portion that extends from a portion of the wall member.

13. The apparatus of claim 8, wherein the conduit includes a liquid fraction enhancement structure and the probe portion is disposed at the liquid fraction enhancement structure, wherein the liquid fraction enhancement structure is a pipe end cap or a blind flange.

14. The apparatus of claim 8, wherein the conduit includes a liquid fraction enhancement structure and the probe portion is disposed at the liquid fraction enhancement structure, wherein the liquid fraction enhancement structure is a horizontal blind-tee coupled to a vertical pipe section.

15. The apparatus of claim 14, wherein the open-ended microwave probe assembly is located in a first portion of the vertical pipe section or is located in a second portion of an inlet or a convergent section of a vertical Venturi device.

16. The apparatus of claim 8, wherein the open-ended microwave probe assembly is located in a first portion of a Venturi device on a throat or divergent section thereof, and the probe portion has a wall member that surrounds a distal end of the probe portion and has a wall portion that extends from a portion of the wall member.

17. The apparatus of claim 8, wherein the conduit comprises a multiphase flowmeter based on microwave transmission-resonance measurement, electrical impedance measurement, X-ray or gamma-ray measurement, or a combination thereof.

18. A device, comprising:
a probe portion, wherein the probe portion comprises a central bore with a conductor and a pressure-resistant insulator surrounding the conductor; and
a connection portion coupled to the probe portion, wherein the conductor extends from an opening at a first distal end of the probe portion into the connection portion, wherein the connection portion comprises a connector coupled to a second distal end of the connection portion, wherein the connection portion comprises a seal face with a groove extending around the probe portion; and
a removable wall member coupled to a proximate end of the probe portion and extending from the proximate end of the probe portion to create a turn in flow of liquid so as to encourage the liquid to collect near the proximate end of the probe portion.

19. The device of claim 18, wherein the removable wall member is disposed at an angle to an axial direction with respect to the probe portion.

20. The device of claim 18, wherein the proximate end of the probe portion comprises a concave surface.

* * * * *